United States Patent [19]

Fishbane

[11] Patent Number: 5,122,145
[45] Date of Patent: Jun. 16, 1992

[54] MEASURING DEVICE FOR USE IN TOTAL HIP REPLACEMENT

[76] Inventor: Bruce M. Fishbane, 1920 Palm Beach Lakes Blvd., Ste. 113, West Palm Beach, Fla. 33409

[21] Appl. No.: 612,606

[22] Filed: Nov. 9, 1990

[51] Int. Cl.[5] ............................................. A61B 17/56
[52] U.S. Cl. .................................................... 606/102
[58] Field of Search ............................. 606/102, 54–59

[56] References Cited

U.S. PATENT DOCUMENTS

| 2,250,417 | 7/1941 | Ettinger | 606/57 X |
| 4,271,832 | 6/1981 | Evans et al. | 606/54 X |
| 4,662,365 | 5/1987 | Gotzen et al. | 606/59 |
| 4,988,349 | 1/1991 | Pennig | 606/59 X |

FOREIGN PATENT DOCUMENTS 214020 3/1968 U.S.S.R. ............................. 606/102

Primary Examiner—Mickey Yu
Assistant Examiner—Kevin G. Rooney
Attorney, Agent, or Firm—Jack N. McCarthy

[57] ABSTRACT

A measuring device and method for use in total hip replacement. A measuring member or arm is pivotally attached to two Steinmann pins in the ilium and a single Steinmann pin is placed in the femur next to the measuring arm. The measuuring arm is made level by the use of a bubble level at a predetermined position and measurements taken to locate the femur with respect to the ilium. This procedure is done after the hip replacement, and measurements taken again. The results are compared to see if the ilium and femur are properly positioned or need adjustment.

8 Claims, 2 Drawing Sheets

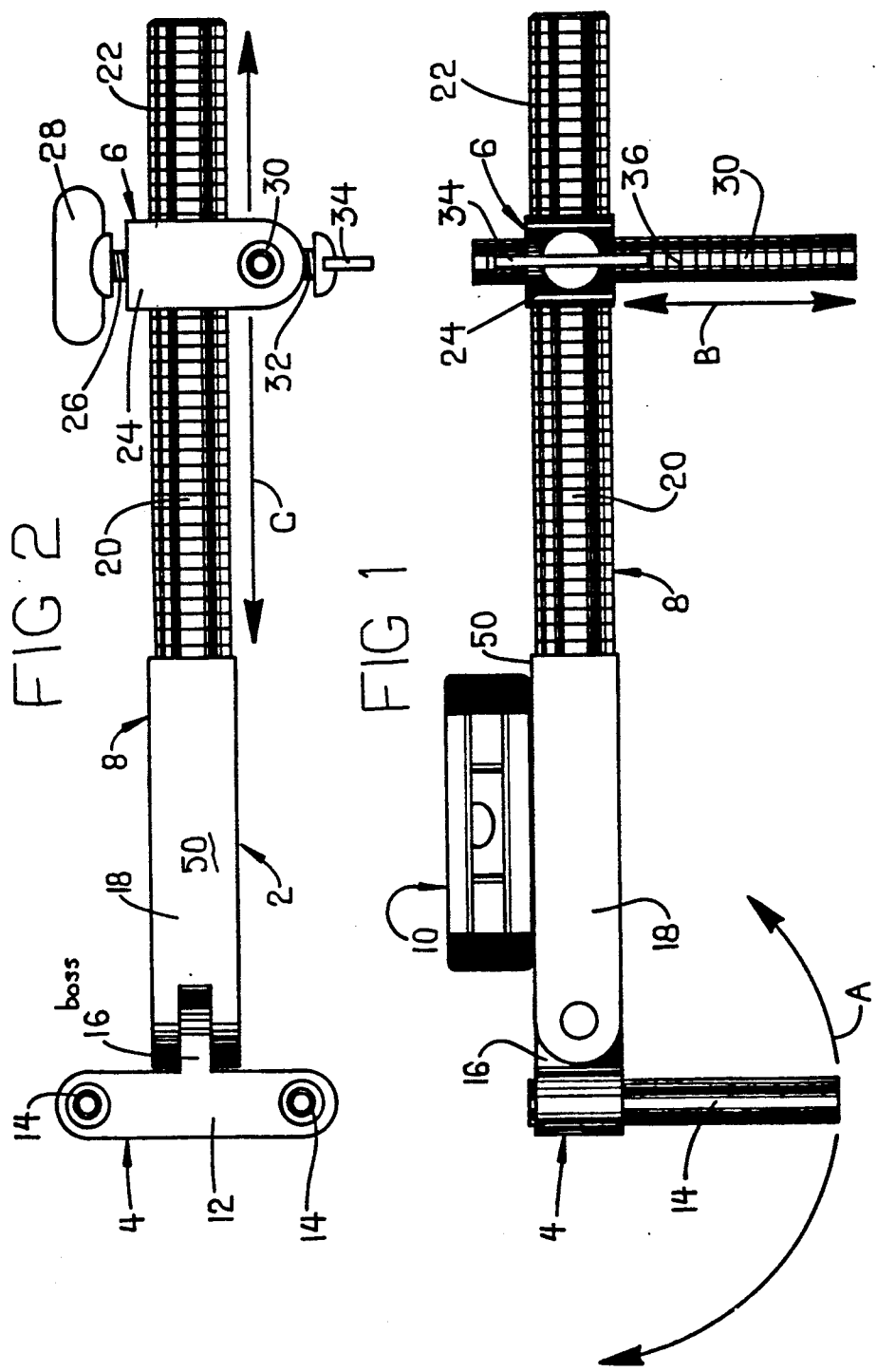

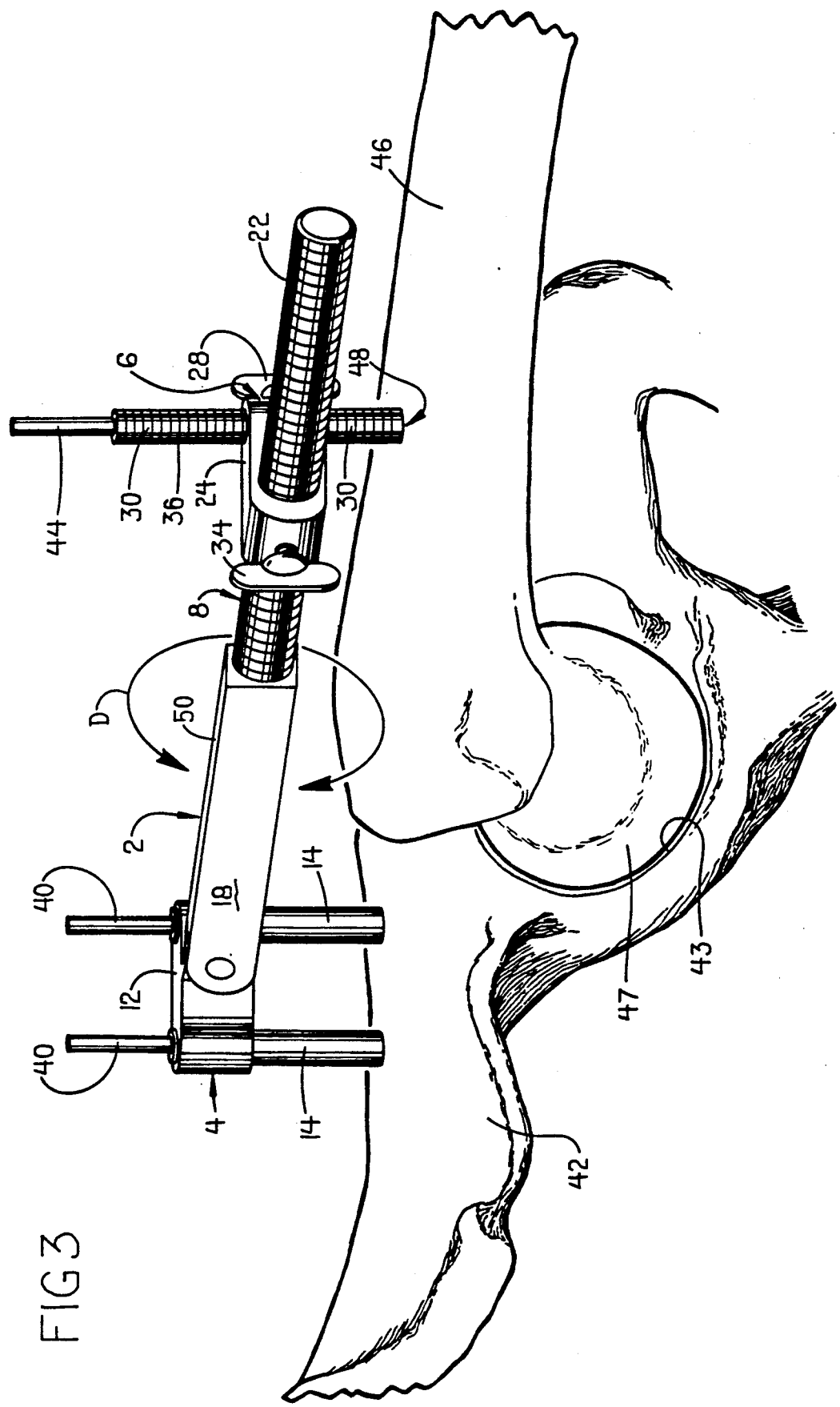

MEASURING DEVICE FOR USE IN TOTAL HIP REPLACEMENT

TECHNICAL FIELD

This device relates to the reproduction of leg length or the accurate alteration of leg length during total hip replacement.

BACKGROUND ART

The reproduction of leg lengths has generally been attempted with the use of single surgical pins and/or tension between the prosthetic components without the availability of an accurate gage to determine variability of leg length.

DISCLOSURE OF INVENTION

An object of this invention is to provide a device with a leveling means which can provide means for assessing the distance between a fixed location in the ilium above the acetabulum (socket) and a fixed location in a proximal femur below the femoral head (ball) prior to dislocation of the pathologic hip for a surgical replacement. This distance defines a base line. After insertion of a total hip replacement, the device is replaced between the fixed location above the acetabulum and the fixed location in the proximal femur, made level as before, and a repeat measurement made. This measurement defines the alteration of relative leg length after insertion of the hip replacement. This replacing of the device also documents any lateral displacement of the femur which occurred during the replacement process.

A further object of this invention is to use a measuring device to connect two disposable surgical pins above the acetabulum as well as a third pin in the proximal femur. Using a bubble level, threedimensional reproduceability of the position of the femur and pelvis is achieved. This device allows for measurement of the relative distance between the fixed surgical pin points accurately measuring pre-and post-replacement length of the lower extremity in the region of the hip, as well as lateral displacement of the femur. The device utilizes a hinged joint between a positioning and measuring arm and the acetabular pins and an adjustable sleeve on the positioning and measuring arm which is placed over the third surgical pin. The top surface of the positioning and measuring arm is designed for use with a bubble level.

Another object of this invention is to provide a method for accurately positioning the ilium and femur for a reproduceable measurement that can be made before and after a total hip replacement. A leveling step provides for properly positioning the femur for the measurements taken. This can be done by placing a level device on the femur and the measurements may be by a ruler.

BRIEF DESCRIPTION OF DRAWINGS

FIG. 1 is a side view of the measuring device including the bubble level;

FIG. 2 is a top view of the measuring device with the bubble level removed, and

FIG. 3 is a perspective view showing the measuring device on an exposed hip prior to dislocation with the Steinmann pins in place

BEST MODE FOR CARRYING OUT THE INVENTION

Reference will now be made in detail to the present preferred embodiment of the invention, an example of which is illustrated in the accompanying drawings.

The measuring device 2 comprises four main parts:
(1) an acetabular guide 4;
(2) an interconnecting measuring member 8;
(3) a femoral guide 6; and
(4) a leveling device 10.

The acetabular guide 4 comprises a bar 12 having a cylindrical pin guide 14 fixed in each end of the bar 12. These cylindrical pin guides 14 extend an equal distance from the bottom side of said bar 12. Cylindrical pin guides 14 cooperate with Steinmann pins 40 set in the ilium 42 above the acetabulum 43 which are hereinafter described. The bar 12 has a boss 16 extending from the center of the side of the bar 90° to the line extending between the centers of the cylindrical pin guides 14. The interconnecting measuring member 8 has one end pivotally connected to said boss 16 for pivotal movement therewith.

The interconnecting measuring member 8 is formed having the one portion 18 connected to said bar 12 square in cross-section for a short distance while the remaining portion 20 is cylindrical. The top surface 50 of the portion 18 of the interconnecting measuring member 8 is flat and adapted to receive the leveling device 10. The surface 50 can have a notch cut therein to retain the small bubble level 10 in place. Bubble level 10 is short and square in cross-section and readable from any of the four sides. Other known means can be used to position and fix the bubble level 10 in place on the interconnecting measuring member 8 if desired. The bubble level 10 is made of plastic with a bubble inside viewable through the side. The end of the portion 18 connected to boss 16 is rounded to permit pivotal movement. The cylindrical portion 20 is marked by measurable circular notches, or scores, 22 along its length for a purpose to be hereinafter described.

The femoral guide 6 comprises a short body member 24 having a first hole drilled therethrough to receive the cylindrical portion 20. This arrangement provides for slidable and rotational movement of short body member 24 on the cylindrical portion 20. A set screw 26 having a butterfly head 28 extends through said short body member 24 so that the end of screw 26 can engage the cylindrical portion 20 when it is manually rotated inwardly, and fix the short body member 24 and cylindrical portion together.

A second hole is drilled through said short body member 24 on one side of said first hole at an angle of 90° to receive a cylindrical pin guide 30. Cylindrical pin guide 30 cooperates with a Steinmann pin 44 set in the femur 46 hereinafter described. The cylindrical pin guide 30 is marked by measurable circular notches, or scores, 36 along its length for a purpose to be hereinafter described. A set screw 32 having a butterfly head 34 extends through said short body member 24 so that the end of screw 32 can engage the cylindrical pin guide 30 when it is manually rotated inwardly, and fix the short body member 24 and cylindrical pin guide 30 together.

In a measuring device 2 constructed, a metal was used which was compatible with known sterilizing methods for surgical instruments. The bubble level 10 was made of a plastic compatible with known sterilizing methods for plastics. This bubble level 10 can also be encased in a sterile disposable cover for use.

Arrows A, B, C and D show relative movement of the components of the measuring device 2. In FIG. 1, arrow A shows the rotational movement of cylindrical pin guides 14 around the end of the interconnecting measuring member 8, and arrow B shows the sliding movement of cylindrical pin guide 30 in the short body member 24 of the femoral guide 6. In FIG. 2, arrow C shows sliding movement of the short body member 24 of the femoral guide 6 on the cylindrical portion 20 of interconnecting measuring member 8. In FIG. 3, arrow D shows the rotational movement of the short body member 24 of femoral guide 6 around the cylindrical portion 20 of the interconnecting measuring member 8. These movements permit the proper positioning of the measuring device 2 by the surgeon when this device is being used for a total hip replacement.

After a patient has been properly prepared with appropriate exposure of the hip for total hip replacement and the supracetabular area has been cleared of muscle, measuring device 2 is placed between the ilium 42 and femur 46 in a position which will provide for proper usage. An ideal situation is when the bottom of the cylindrical pin guides 14 contact the ilium 42 above the acetabulum 43 and the cylindrical pin guide 30 can be positioned to engage the femoral cortex 48 of the femur 46 with the interconnecting measuring member 8 passing freely over any intermediate portions of the femur. The acetabular guide 4 is held in place and the cylindrical pin guides 14 are utilized to position two disposable Steinmann pins 40 into the ilium. These pins 40 are each paced in a drill and extended through a cooperating cylindrical pin guide 14 to be drilled into the outer table of the ilium 42 and tapped by a hammer into the inner table. The pins 40 are then cut above the top of the cylindrical pin guides 14 at the same height. The femur 46 is then rotated to a conveniently reproduceable position and the femoral guide 6 is utilized to place a disposable Steinmann pin 44 into the femur. Pin 44 is placed in a drill and extended through the cylindrical pin guide 30 and drilled and hammered into place as pins 40. It is generally preferable that an attempt is made that all Steinmann pins 40 and 44 be parallel.

The cylindrical pin guide 30 is placed flush against the femoral cortex 48 and a leveling device 10 is positioned on the top surface 50 of the portion 18 of the interconnecting measuring member 8. The leg of the patient is moved, thereby moving the femur 46 to center the bubble of the leveling device 10. Both set screws 26 and 32 are tightened. A measurement is taken, utilizing the circular notches, or scores, 22 to document the distance between the Steinmann pins 40 and Steinmann pin 44 (this measurement can be made by a separate ruler if desired); a measurement is also taken, using the circular notches, or scores, 36 along the cylindrical pin guide 30 to document the distance between the femoral cortex 48 of the femur 46 to the interconnecting measuring member 8 (this measurement can be made by a separate ruler if desired).

The Steinmann pin 44 set in the femur 46 is removed and the measuring device 2 removed by sliding the cylindrical pin guides 14 over the Steinmann pins 40 set in the ilium 42. The total hip replacement is performed involving the use of a new acetabulum cup and femur ball. Upon completion of the total hip replacement, the set screws 26 and 32 are loosened and the acetabular guide 4 has its cylindrical pin guides 14 placed over the Steinmann pins 40 and the Steinmann pin 44 is reinserted into the previously made drill hole in the femur 46 with the cylindrical pin guide 30 placed over the Steinmann pin 44. The cylindrical pin guides 14 and the cylindrical pin guides 30 are paced in the $same position they were in when the original measurements were taken. In this example, the bottoms of the cylindrical pin guides 14 were against the ilium and the bottom of the cylindrical pin guide 30 was against the femoral cortex 48. The bubble level 10 on the interconnecting measuring member 8 (either attached thereto or placed on the top surface 50 of the portion 18) is made to indicate level by movement of the leg of the patient so that the interconnecting measuring member 8 is level as in the original measurement, the thumb screws 26 and 32 are again tightened and measurements ascertained as above. If it was desirable to reproduce the original measurements with the reconstructed hip, these new measurements should be equal to the original measurements, or only have a difference so negligible that no further adjustments to lengthen, shorten, lateralize, or medialize the femur, are needed. However, when the patient has a leg length discrepancy before the hip reconstruction, and a lengthening or shortening of the leg is to be obtained as a result of the hip reconstruction, this measuring device 2 will document the differential measurement of the reconstructed hip to determine if a proper change exists or if an adjustment is necessary. Here again, these adjustments are generally made within the prosthesis. If measurements indicate a need for adjustment, these are made to achieve proper positioning of the new femur ball. After an adjustment, the procedure for using the measuring device 2 can be used again to see if the measurements now obtained are within acceptable limits from the original measurements.

It is noted that if the length of the cylindrical pin guides 14 is too short to reach the ilium for a particular patient to permit the interconnecting measuring member 8 to properly extend to a position over the femur 46, the Steinmann pins 40 can be cut an extra amount above the top of the cylindrical pin guides 14 so that the top of the cylindrical pin guides 14 can be placed at the tops of the Steinmann pins 40 to serve to locate the acetabular guide 4 in measuring so that its position can be accurately reproduced later.

While the principles of the invention have now been made clear in an illustrative embodiment, it will become obvious to those skilled in the art that many modifications in arrangement are possible without departing from those principles. The appended claims are, therefore, intended to cover and embrace any such modifications, within the limits of the true spirit and scope of the invention.

I claim:

1. A device for use in total hip replacement including an acetabular guide, said acetabular guide having a short bar with a first pin guide on each end for engagement with two Steinmann pins extending from the ilium, a measuring arm member, means pivotally connecting said measuring arm member at one end to said short bar between said pin guides, a femoral guide, said femoral guide having a short body member, means slidably and rotatably mounting said short body member on the free end of said measuring arm member, said short body member having a third pin guide, said third pin guide being a sleeve, means slidably mounting said sleeve in said short body member at an angle of 90° with said measuring arm member for engagement with a Steinmann pin extending form the femur, means being provided to fix said femoral guide in a desired position on said measuring arm member, and means being provided to fix said sleeve in a desired position in said short body member.

2. A combination as set forth in claim 1 wherein said measuring arm member is adapted to receive a level device.

3. A combination as set forth in claim 1 wherein said measuring arm member has a small bubble level thereon.

4. A combination as set forth in claim 1 wherein said third pin guide is marked to accurately record the position of the third pin guide in said short body member when desired.

5. A combination as set forth in claim 1 wherein said measuring arm is marked to accurately record the position of said femoral guide when desired, and said third pin guide is marked to accurately record the position of the third pin guide in said short body member when desired.

6. A method of positioning and reproducing the positioning of the ilium and femur in total hip replacement by:
   (1) exposing the ilium and femur for total hip replacement;
   (2) placing two Steinmann pins in the ilium above the acetabulum on a line approximately 90° to the length of the femur;
   (3) placing the femur in a reproduceable position;
   (4) placing one Steinmann pin in the femur along its length below the femoral head;
   (5) connecting said two Steinmann pins in the ilium at a known height and the one Steinmann pin in the femur by an adjustable arm device;
   (6) leveling the position of the adjustable arm device to reproduce its position;
   (7) measuring the distance between said one Steinmann pin and the two Steinmann pins while the position of the adjustable arm device is level;
   (8) measuring the distance between the adjustable arm device at the one Steinmann pin from the femur while the position of the adjustable arm device is level;
   (9) removing the one Steinmann pin in the femur and adjustable arm device;
   (10) performing the total hip replacement involving the insertion of a new acetabular cup and femur ball;
   (11) replacing the one Steinmann pin in the femur and adjustable arm device on the two Steinmann pins and one Steinmann pin as in step (5);
   (12) leveling the position of the adjustable arm device as in step (6);
   (13) measuring the distance between said one Steinmann pin and the two Steinmann pins while the position of the adjustable arm device is level;
   (14) measuring the distance between the adjustable arm device at the one Steinmann pin from the femur while the position of the adjustable arm device is level;
   (15) comparing the measured distances in steps (7) and (8) to the measured distances in steps (13) and (14) to see if the original position of the ilium and femur has been reproduced.

7. A method as set forth in claim 6 wherein if the original position of the ilium and femur is not substantially reproduced the following step is taken:
   (16) adjusting the prosthesis to alter the positioning of the femur so that the original position of the ilium and femur is substantially reproduced.

8. A device for use during a total hip replacement operation including an acetabular guide, said acetabular guide having one short bar, said bar having a first and second pin guide, each pin guide extending from each end of said bar for positioning over two Steinmann pins extending form the ilium, said short bar having a boss extending from a midportion thereof between said first and second pin guides at an angle of 90°, a measuring arm member, means pivotally connecting said measuring arm member at one end to said boss to pivot thereon, a femoral guide, said femoral guide having a short body member, means slidably and rotatably mounting said short body member on the free end of said measuring arm member, said short body member having a third pin guide, means slidably mounting said third pin guide in said short body member at an angle of 90° with said measuring arm member for positioning over a Steinmann pin extending from the femur, means being provided to fix said femoral guide in a desired position on said measuring arm member, and means being provided to fix said third pin guide in a desired position on said short body member.

* * * * *